United States Patent
Cole et al.

(10) Patent No.: US 9,926,052 B2
(45) Date of Patent: Mar. 27, 2018

(54) CONTROL MECHANISM FOR TRANSFORMER IN-SITU INSPECTION DEVICE

(71) Applicant: ABB TECHNOLOGY AG, Zurich (CH)

(72) Inventors: Gregory A. Cole, West Hartford, CT (US); Gregory F. Rossano, Enfield, CT (US); William Eakins, Bloomfield, CT (US); Daniel T. Lasko, Bloomfield, CT (US); George Zhang, Windsor, CT (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 14/983,638

(22) Filed: Dec. 30, 2015

(65) Prior Publication Data
US 2017/0190396 A1 Jul. 6, 2017

(51) Int. Cl.
| B63B 39/02 | (2006.01) |
| B63B 35/00 | (2006.01) |
| G01N 21/954 | (2006.01) |
| G01N 21/90 | (2006.01) |

(52) U.S. Cl.
CPC .............. *B63B 39/02* (2013.01); *B63B 35/00* (2013.01); *G01N 21/9072* (2013.01); *G01N 21/954* (2013.01); *G01N 2201/0221* (2013.01); *G01N 2201/12* (2013.01)

(58) Field of Classification Search
CPC ......... B63B 39/00; B63B 39/02; B63B 43/08; B63B 35/85; B63B 3/00; B63B 3/13; B63B 59/00; B63B 59/08; B63B 59/10; B63H 5/00

USPC ................................. 114/124, 222, 312
See application file for complete search history.

(56) References Cited

U.S. PATENT DOCUMENTS

| 4,455,962 A * | 6/1984 | Gongwer ................. B63H 5/00 |
| | | 114/124 |
| 4,713,030 A | 12/1987 | Ingle |
| 4,964,356 A * | 10/1990 | Sullivan ................... B63G 8/42 |
| | | 114/124 |
| 5,018,472 A * | 5/1991 | Sullivan ................... B63G 8/42 |
| | | 114/124 |
| 5,052,932 A | 10/1991 | Trani |
| 6,499,712 B1 | 12/2002 | Clark et al. |
| 2001/0003963 A1 | 6/2001 | Chaix |
| 2014/0033961 A1 | 2/2014 | de Troz |

(Continued)

FOREIGN PATENT DOCUMENTS

DE    202010011793 U1    2/2011

OTHER PUBLICATIONS

Patent Cooperation Treaty, International Search Report cited in co-pending PCT Appln. No. PCT/US16/69545, dated Mar. 16, 2017 (2 pages).

(Continued)

*Primary Examiner* — Lars A Olson
(74) *Attorney, Agent, or Firm* — Taft Stettinius & Hollister LLP

(57) ABSTRACT

An inspection device for use in a fluid container includes a hull adapted to be received in the fluid container and a control mechanism carried by the hull. The control mechanism movably positions a weight about the hull so as to adjust an angular orientation of the hull within the fluid container.

20 Claims, 13 Drawing Sheets

(56) References Cited

U.S. PATENT DOCUMENTS

2014/0202367 A1 7/2014 Dollar
2015/0369751 A1 12/2015 Cheim et al.
2016/0129979 A1 5/2016 Rossano et al.

OTHER PUBLICATIONS

Patent Cooperation Treaty, Written Opinion cited in co-pending PCT Appln. No. PCT/US16/69545, dated Mar. 16, 2017 (9 pages).

\* cited by examiner

CONTROL MECHANISM FOR TRANSFORMER IN-SITU INSPECTION DEVICE

TECHNICAL FIELD

Generally, the present invention is directed to transformer inspection systems. Specifically, the present invention is directed to a remotely controlled inspection device inserted into a liquid-filled container, such as a high-voltage transformer. More particularly, the present invention is directed to a remotely controlled inspection device which includes a control mechanism to assist with orientation and balancing of the device.

BACKGROUND ART

Liquid-filled power transformers are one of the key components in power transformation and distribution. The liquid is used to cool the internal components of the transformer during its operation. As is well understood, the large liquid-filled power transformers are extremely heavy and difficult to transport and replace. They have a limited life span and necessary maintenance and repair are needed periodically.

While non-invasive techniques are now used to identify potential problems that the transformer may have; the common way to directly observe the windings, cables, supports and connectors inside a transformer tank is to drain the liquid from the transformer tank and send in a person through a manhole or open the transformer tank by cutting a top plate from the tank. Therefore, there is a need in the art for a device and related method for in-situ inspection of a transformer. To assist in the operation of such a device, there is also a need to provide a control mechanism that assists in the orientation and balancing of the device.

SUMMARY OF THE INVENTION

In light of the foregoing, it is a first aspect of the present invention to provide a control mechanism for transformer in-situ inspection device.

It is another aspect of the present invention to provide an inspection device for use in a fluid container, comprising a hull adapted to be received in the fluid container, and a control mechanism carried by the hull, the control mechanism movably positioning a weight about the hull so as to adjust an angular orientation of the hull within the fluid container.

BRIEF DESCRIPTION OF THE DRAWINGS

These and other features and advantages of the present invention will become better understood with regard to the following description, appended claims, and accompanying drawings wherein:

BEST MODE FOR CARRYING OUT THE INVENTION

Figure 1:
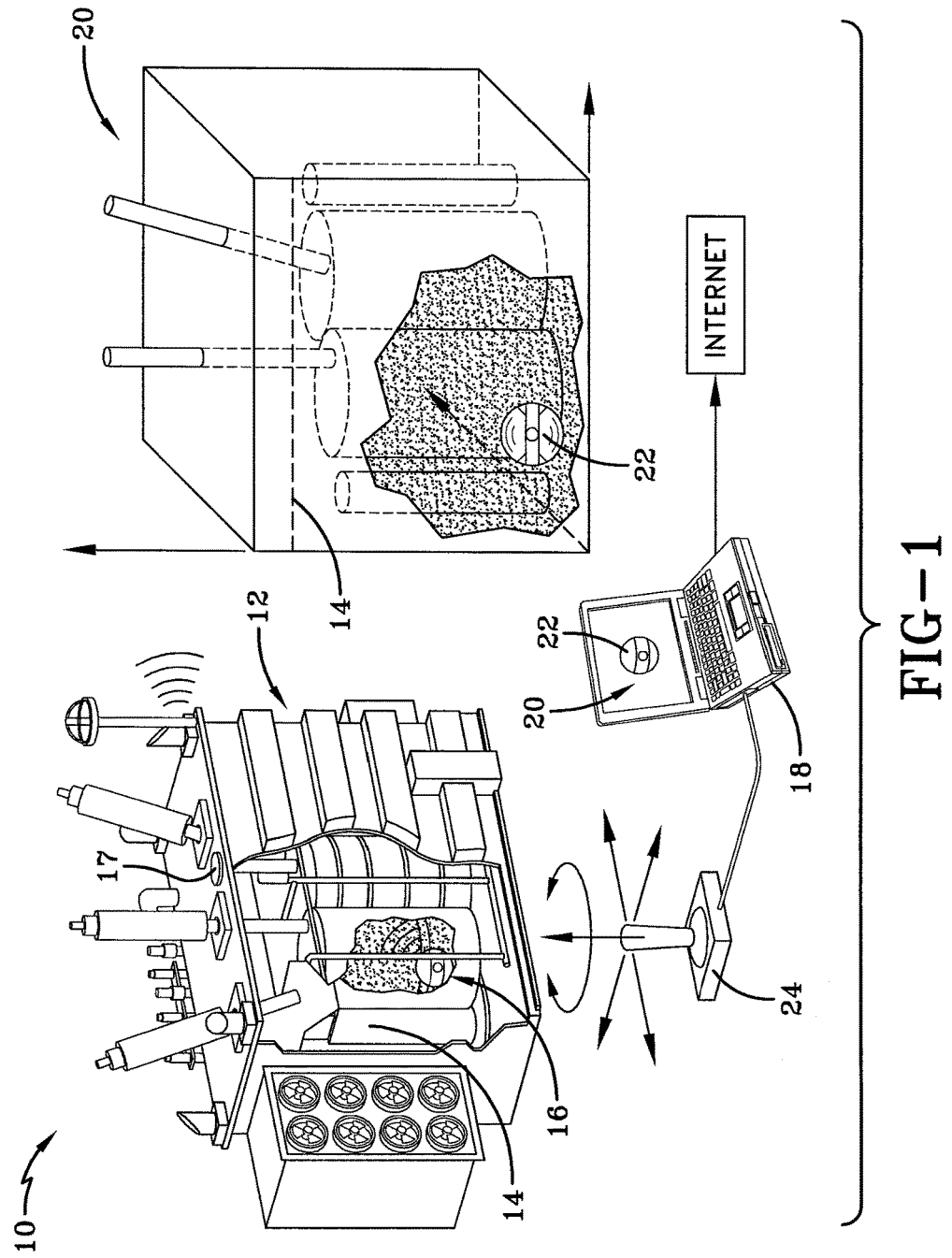
FIG. 1 is a schematic diagram of a system for transformer in-situ inspection according to the concepts of the present invention.

Referring now to the drawings, and in particular to FIG. 1, it can be seen that a system for transformer in-situ inspection is designated generally by the numeral 10. In most embodiments, the system 10 is utilized for the inspection of a transformer 12 which contains high-voltage electrical components immersed in a cooling fluid 14 such as oil. Skilled artisans will appreciate that the inspection occurs only when the transformer is off-line or not in use. The transformer 12 utilizes the cooling fluid 14 to maintain and disperse heat generated by the internal components during operation of the transformer. Although the present embodiment is directed to systems for inspecting electrical transformers, it will be appreciated that the teachings disclosed herein are applicable to any inspection device used in a relatively large volume container, which may or may not be sealed, which maintains a fluid. In some embodiments, the fluid used in the transformer includes dielectric properties. As skilled artisans will appreciate, the transformer 12 is maintained in a sealed configuration so as to prevent contaminants or other matter from entering. As used herein, a "sealed configuration" of the tank allows for sealed conduits and/or ducts to be associated with the transformer's tank or housing to allow for connection to the electrical components and/or monitoring devices maintained in the tank. The tank is also provided with at least one opening to allow for the filling and/or draining of the cooling fluid.

An inspection device designated generally by the numeral 16 is insertable into the transformer 12 or sealed container and is movable utilizing un-tethered, wireless remote control. As will be discussed in further detail as the description proceeds, the device 16 includes a control mechanism to assist in the orientation and balancing of the device while immersed in the cooling fluid. The transformer 12 has at least one transformer hole 17. In general operation, the oil is inserted through any number of holes located in the top of the tank. Holes 17 may also be provided at the bottom of the tank to allow for the fluid to be drained. The holes 17 are provided with the appropriate plugs or caps. Accordingly, it will be appreciated that the size of the inspection device must be such that it can fit within the hole 17.

A computer 18, such as a laptop computer or other appropriate computing device, is in wireless communication with the inspection device 16. The computer 18 may maintain a virtual transformer image 20 of the internal construction of the transformer. The computer 18 may utilize the virtual transformer image 20 in conjunction with a virtual inspection device 22, which represents the actual inspection device 16, so as to monitor the positioning of the device 16 within the transformer 12. A motion control input device, such as a joystick 24 is connected to the computer 18 and allows for a technician to control movement of the device 16 inside the transformer 12 by observing the virtual inspection device 22 as it moves about the virtual transformer image 20. In other words, the technician may control movement of the device 16 based on the device's observed or detected position within the transformer 12. Other types of motion control input devices, such as used in video games, handheld computer tablets, computer touch screens or the like may be employed. Other embodiments of the inspection device 16 may allow for line of sight control where a technician directly views a camera and/or sensor-generated images from the device and provides input to thrusters and/or other control mechanisms to propel and steer the device.

Figure 2:
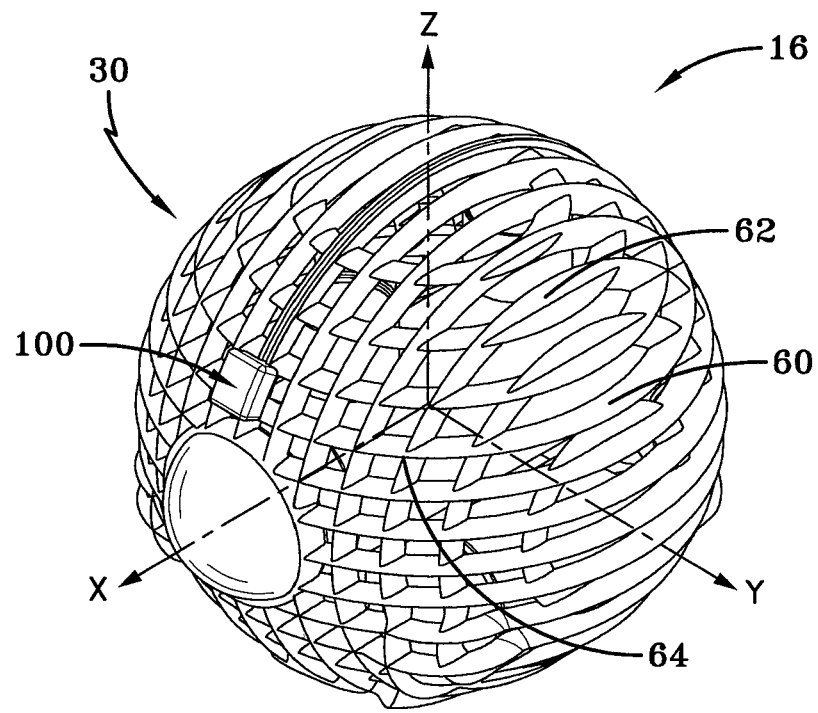
FIG. 2 is a perspective view of an inspection device showing a control mechanism according to the concepts of the present invention.
Figure 3:
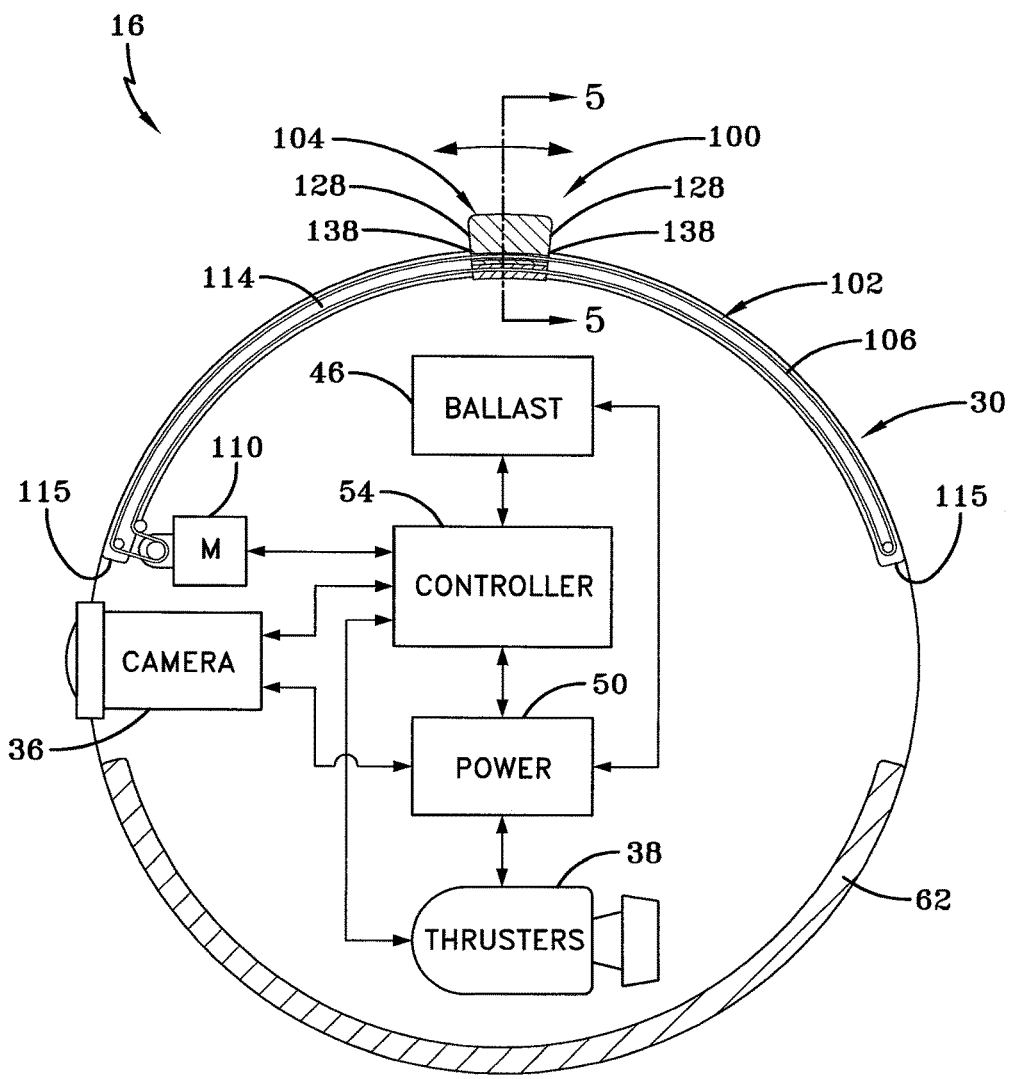
FIG. 3 is a schematic diagram of the inspection device according to the concepts of the present invention.
Figure 4:
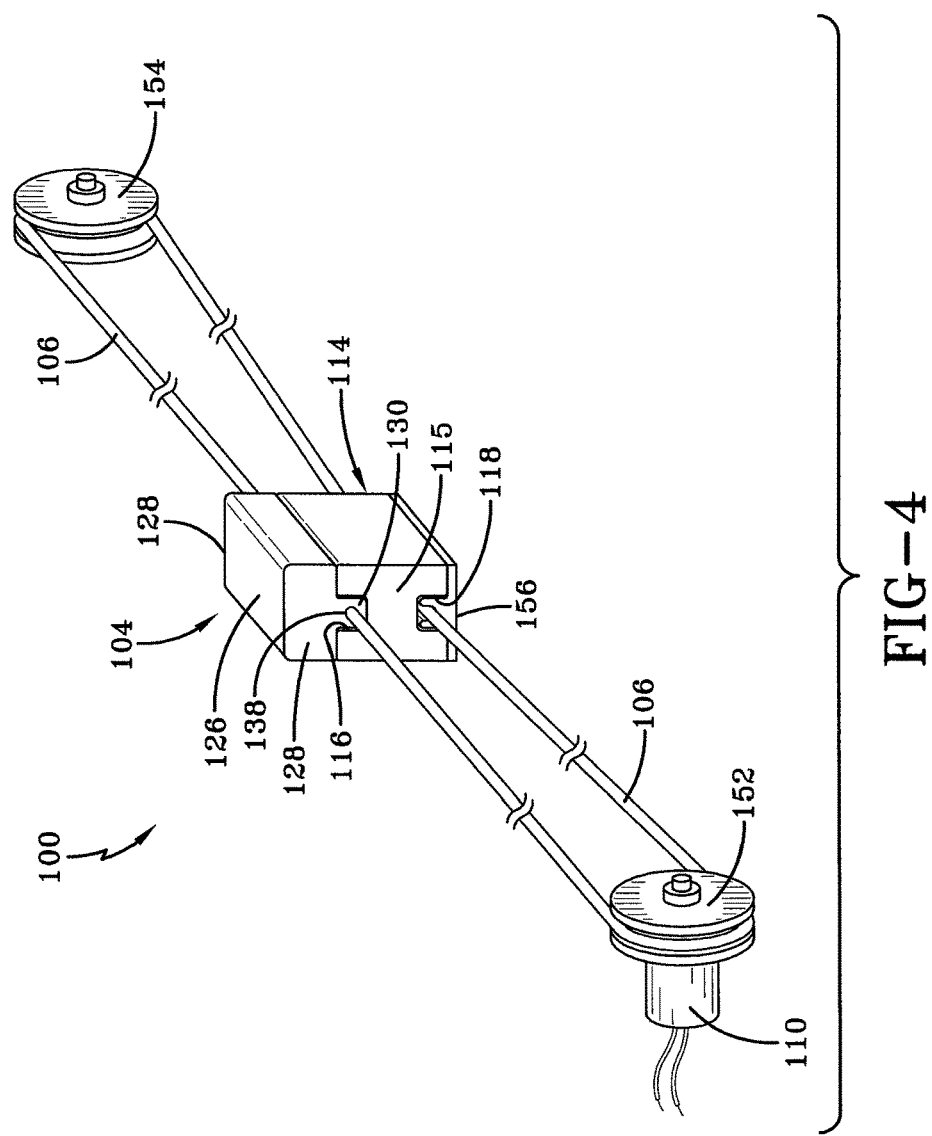
FIG. 4 is a partial schematic of the control mechanism used with the inspection device according to the concepts of the present invention.

As best seen in FIGS. 2-4, the inspection device 16 includes a hull 30. The hull, which may be referred to as a cage hull or a housing, is of a substantially cylindrical or spherical rounded construction with no significant protrusions or extensions that might otherwise become entangled with the internal components within the transformer. The hull 30 covers or effectively protects the internal components of the device which are utilized to facilitate operation of the device. The cage hull 30, which may also be considered a grid-style hull, may include at least one sensor 36 such as a camera which may remotely transmit pictures or video to a technician for evaluation. The sensors may also include, but are not limited to, temperature sensors, viscosity sensors to detect specific materials and the like. Maintained by the cage hull 30 is at least one directional thruster 38 which when actuated generates a thrust vector so as to move the hull 30 in a desired direction.

Ballast devices 46 may be provided within the cage hull 34 so as to control the equilibrium positioning of the device. In other words, control of the ballast allows the device's natural buoyancy to be controlled as deemed appropriate by the technician. A power compartment 50 may be maintained within the hull 30 and is utilized to carry the batteries that power the various components within the device. These components may include the various sensors, the ballast devices, the thrusters and in particular the motors or pumps utilized to operate the thrusters. At least one light may be provided so as to illuminate the immediate area of the device. A controller 54 may be provided in the device which contains the electronics and control devices utilized to operate the various sensors, thrusters, lights and other components of the device. The light, and the electronics and control devices, may be powered by the batteries carried in the power compartment. Skilled artisans will appreciate that selective control of the thrusters in either the appropriate direction allows for movement of the device in six degrees of freedom within the transformer.

The cage hull 30 may be constructed from at least one bar 60 oriented in a first orientation and at least one second bar 62 oriented in a second orientation. At a minimum, the bar 60 and bar 62 intersect with one another at an intersection point 64. The bars 60 and 62, which have openings therethrough, form the cage hull 30 such that the internal components are internally maintained within the inner periphery of the bars 60 and 62. Although two orientations of the bars 60 and 62 are shown, skilled artisans will appreciate that the bars could be spaced and/or positioned in three or more orientations.

Other embodiments of the inspection device 16 may utilize other hull configurations. For example, instead of utilizing a cage hull configuration as described, the hull may be provided with a continuous uniform surface, of any shape, which provides the necessary openings as needed for the thrusters, sensors, and the like. In other embodiments, any combination of a continuous uniform surface and grid-like configuration may be used for the hull.

Generally, all the embodiments of the present invention are directed to moving a mass, with a predetermined weight, within or about the hull. The mass, as will be discussed, may take many different forms and is distinguishable from the ballast devices 46 previously disclosed. As noted, the ballast devices, as controlled by the controller 54, are employed to adjust the buoyancy of the inspection device. Increasing the ballast effectively lowers the device in the fluid container. Reducing or releasing the ballast allows the device to ascend within the fluid container. If no other forces are acting upon the device, adjusting the amount of ballast in the device, as used in this description, moves the device in a substantially vertical direction. As used herein, the mass may refer to a weight in the form of a solid material or a fluid in the form of a liquid, gas or combination thereof. By adjusting the position or density of the mass in or about the hull, the hull is re-oriented or tilted while remaining in relatively the same position. This re-orientation permits a sensor to be pointed in a desired direction so as to observe a particular item within the fluid container. In the embodiments disclosed, movement of the mass and the associated mechanisms is done in such a way to not interfere with other components maintained in the inspection device 16. In other words, the components of the inspection device allow free and uninterrupted movement of the mass in its various forms. Additionally, all the embodiments disclosed herein may employ the sensors, the controller 54, the power 50, the thruster(s) 38, the camera 36, and other components. The primary difference between the embodiments is the position of the mass and configuration of a mechanism to move the mass as will be discussed. Variations to the aforementioned components and the hull may be made to accommodate variations in the mechanism that moves the mass.

Referring now to FIGS. 2-7, it can be seen that a control mechanism designated generally by the numeral 100 is carried by the hull 30. A portion of the control mechanism 100 may be externally positioned; however, some components are maintained internally of the hull. Skilled artisans will appreciate that the control mechanism 100 could be linear in configuration, but in this embodiment the mechanism is curvilinear and is coincident with the curvature of the hull 30. And although only a single control mechanism 100 is shown, skilled artisans will appreciate that multiple control mechanisms may be employed.

As schematically shown in FIG. 3 and as illustratively shown in FIG. 2, the control mechanism 100 provides a rail 102 which may be carried specifically by the bar 62 that is centrally positioned and vertically aligned, or in some embodiments the rail 102 may replace the centrally positioned bar. In most embodiments the rail 102 is the bar 62 having the largest radius, but other bars with a smaller radius may be employed. A weight 104, which is a predetermined amount of mass, is carried by and moves along the rail 102 by way of a wire loop 106 that is connected to each end of the weight 104. A motor 110, which may be mounted on or about the rail 102 and/or which may be mounted internally within the hull, is coupled to the wire loop 106 and also connected to the controller 54. In operation, the controller 54 sends instructions to the motor 110 which moves the weight along the rail so as to change the tilt angle of the hull. As will be discussed, movement of the weight directs or changes the orientation of the hull and associated sensors to a desired line of sight. In other words, the sensors, such as the camera, are oriented to view a specific area within the transformer or other enclosure.

Figure 5:
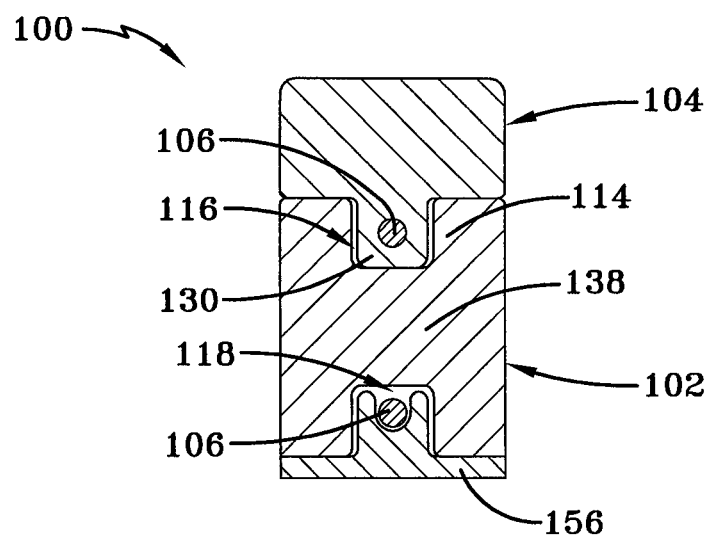
FIG. 5 is a cross-sectional view taken along lines 5-5 of FIG. 3 showing a weight used in the control mechanism according to the concepts of the present invention.

As best seen in FIGS. 3 and 5, the rail 102 may have an H shaped cross-section. The rail 102 provides for a bar 114 which has opposed ends 115. The bar 114 may include a bar groove 116 on an externally facing top side and may also have a corresponding bar groove 118 on an opposite or internally facing bottom side.

The weight 104 includes a body 126 which has opposed ends 128. Extending from an underside of the body 126 is a bar rib 130 which may be sized to be slidably received and slidably moveable in the bar groove 116.

The wire loop 106, which may be constructed of a flexible, high-tensile strength material, is connected to the weight 104. The wire loop 106 provides for loop ends 138 wherein each loop end is connected to a corresponding opposed end 128 of the body 126. As shown in the drawings, the loop ends 138 are connected to end surfaces of the bar rib 130 such that the wire loop 106 is received in the corresponding bar grooves 116 and 118. In some embodiments the loop ends 138 may be connected to the body 126 above the bar rib 130.

The motor 110 may be mounted to the bar 114 or may be positioned in close proximity to the bar. The motor 110 is connected to the controller 54 and the power component 50. As a result, the controller 54, upon receiving or generating an appropriate instruction, can control operation of the motor to rotate a reversible motor shaft (not shown) in either direction and at a desired speed. As best seen in FIG. 4, the motor shaft is connected to a motor wheel 152 and rotated thereby. Wrapped around the motor wheel 152 is the wire loop 106. The wire loop 106 may be wrapped around the motor wheel at least two times. At an opposite end of the bar 114 is rotatably mounted a back wheel 154 which also receives the wire loop 106 wrapped around at least once. In some embodiments a loop retainer 156 may be coupled to the bar 114. The loop retainer 156 at least partially encloses the bar groove 118 so as to keep the loop within the groove and prevent entanglement with other components.

In operation, as the motor rotates the motor wheel 152, the loop 106 moves the attached weight 104 along the rail in the corresponding direction. As best seen in FIG. 5, the bar rib 130 is received in the top groove and slides along the facing surfaces of the rail 102. It will further be appreciated that the wire loop 106, based upon its connection to the bar rib 130, is received in the groove 116 and, as such, is retained so as to not migrate away from the bar 102. Moreover, as the loop 106 traverses on the underside of the bar 102 the loop is received in the bottom groove and may be retained by the retainer 156. The retainer 156 may be provided in an entire length section or may be provided in strategically placed positions so as to ensure that the loop 106 is retained within the groove 118.

Figure 7:
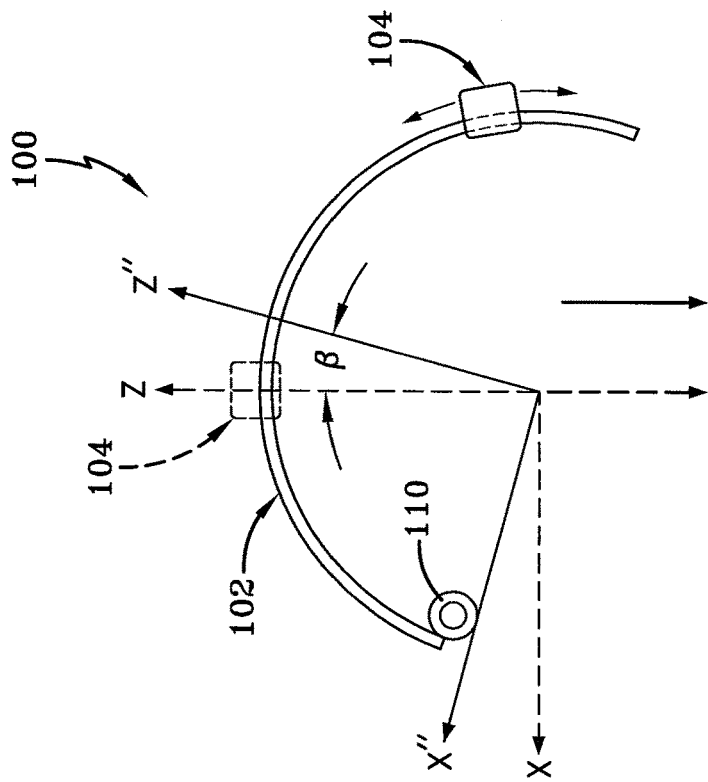
FIG. 7 is a schematic representation of the weight on the inspection device in a second position according to the concepts of the present invention.
Figure 6:
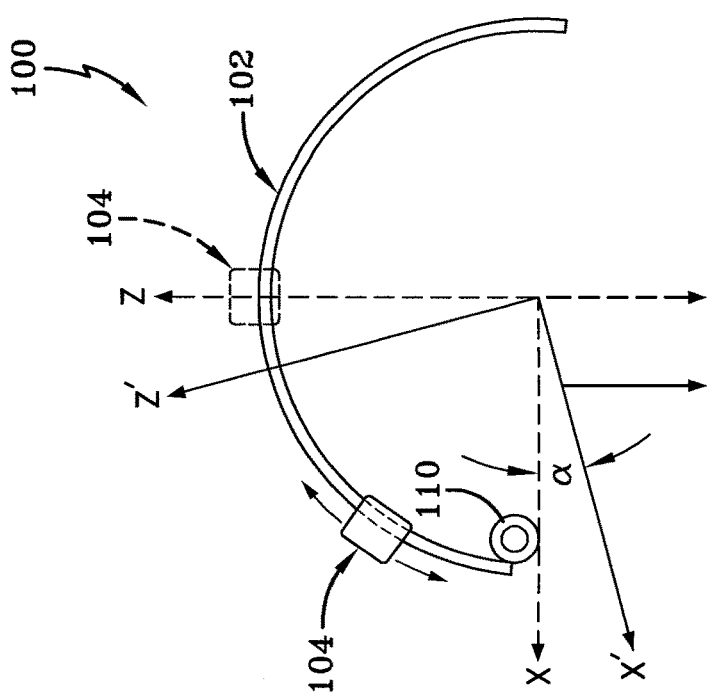
FIG. 6 is a schematic representation of the weight on the inspection device in a first position according to the concepts of the present invention.

Referring now to FIGS. 6 and 7, it can be seen that movement of the weight 104 along the bar 102 may be used to change the orientation of the hull 30. For example, as seen in FIG. 6, the tilt angle is adjusted by sliding or otherwise moving the weight along the rail on top of the hull structure. Normally the weight is placed such that the center of gravity aligns with the center of buoyancy of the craft creating a vertical orientation of the craft with the main camera or other sensor pointing horizontally. When it is desired to tilt the central line of the camera or other sensor down, the weight is slid to a forward position as shown in FIG. 6. As a result, the center of gravity is moved to the front (from X axis to X' and Z to Z') by a distance. Since the center of buoyancy is acting upward (not shown in the Fig.), the sensor/camera is tilted downward at an angle $\alpha$. When the weight is slid backward, as shown in FIG. 7, the sensor/camera is tilted upward with an angle $\beta$ (from X to X" and Z to Z"). As previously discussed, the weight location is adjusted by using the motor with the wire loop to pull the weight in either direction. The motor rotates the motor wheel 152 which has the loop wound upon it. The weight slidably moves upon the rail surface and, in the embodiment shown, along the top groove. In this way, the weight's position may be controlled by the motor which is controlled by the controller 54.

By utilizing the weight in the manner described, more precise control of the hull and the inspection device can be obtained. As a result, the use of the power thrusters or other mechanisms that are utilized to move the inspection device are not required to orient the sensor in a different direction or orientation. Another advantage of the present embodiment is that the weight can be maintained externally of the hull so as to maximize interior space for the other components utilized by the inspection device. Moreover, the configuration of the control mechanism 100 is of a relatively low profile and will not interfere with the movement of the hull or inspection device within the fluid material. And, if needed, the control mechanism provides for a way to easily correct the balance of the device in the event balance issues arise.

Figure 8:
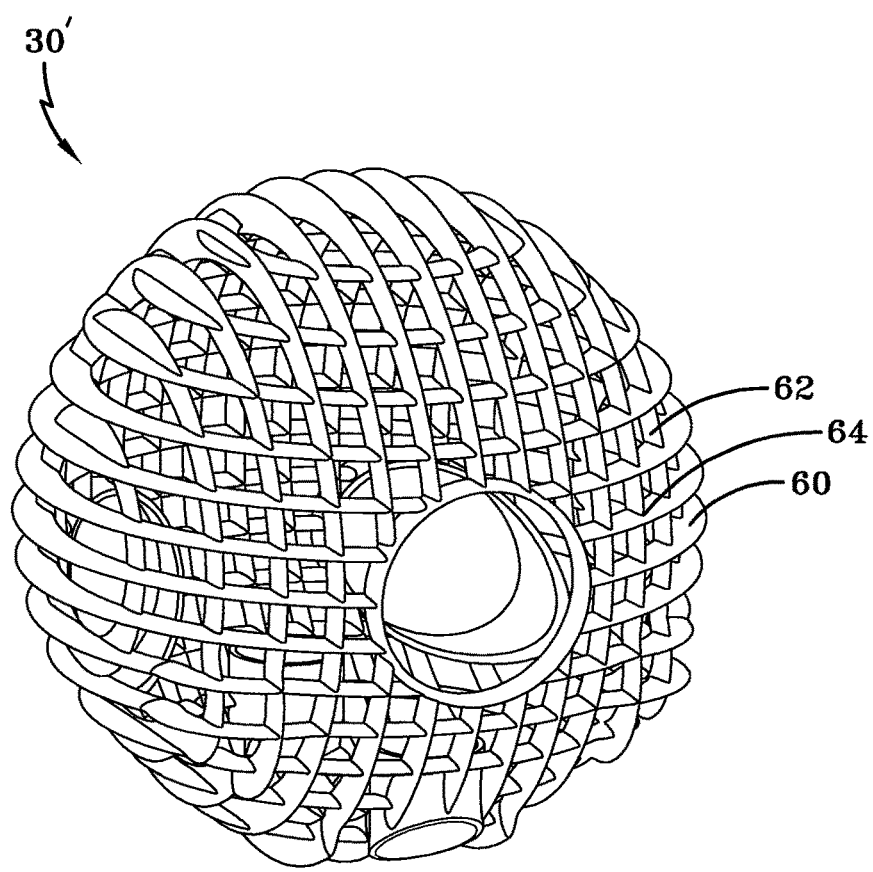
FIG. 8 is a perspective view of an alternative embodiment of an inspection device hull according to the concepts of the present invention.
Figure 9:
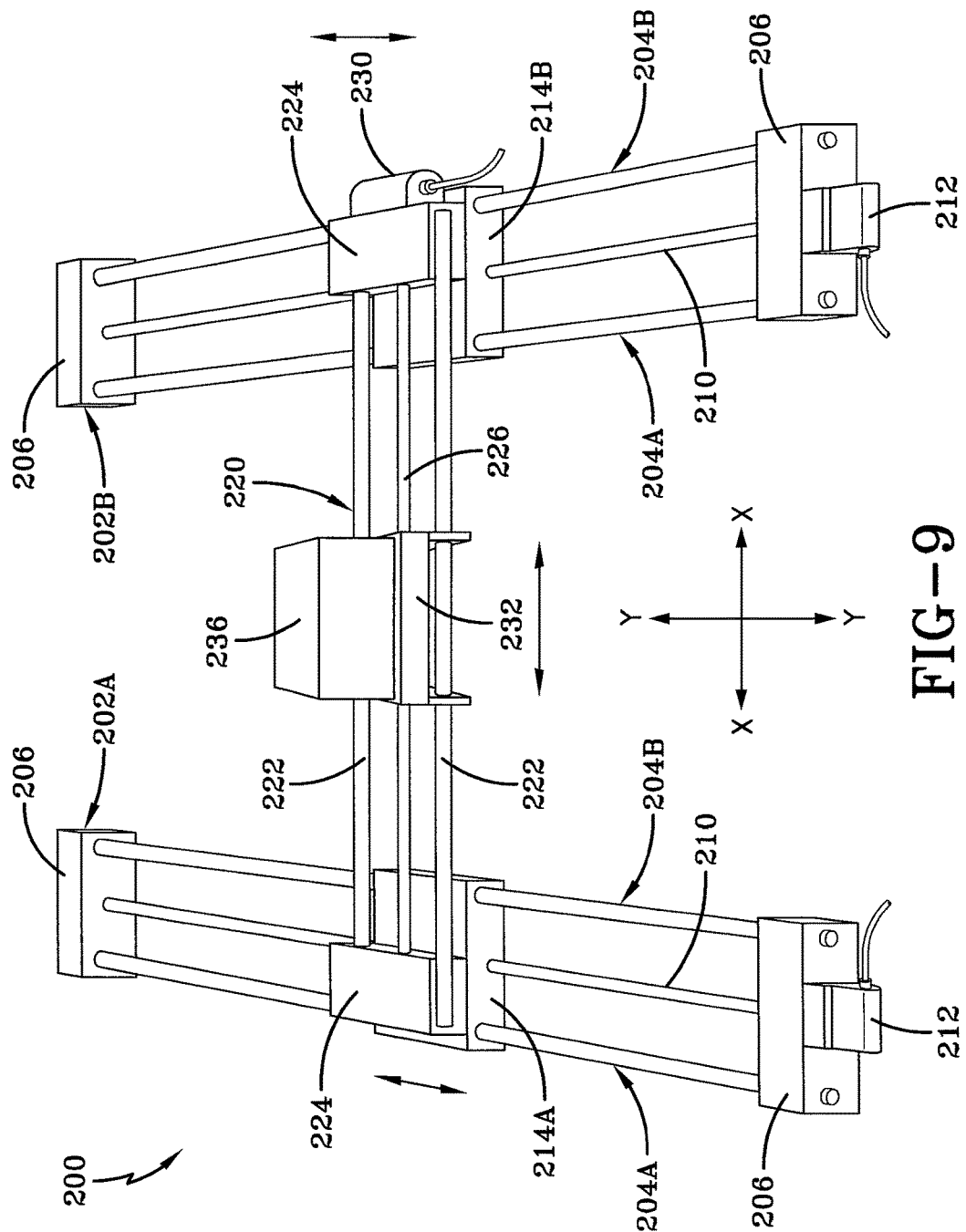
FIG. 9 is a perspective view of an alternative control mechanism used in the alternative embodiment of the inspection device hull according to the concepts of the present invention.
Figure 10:
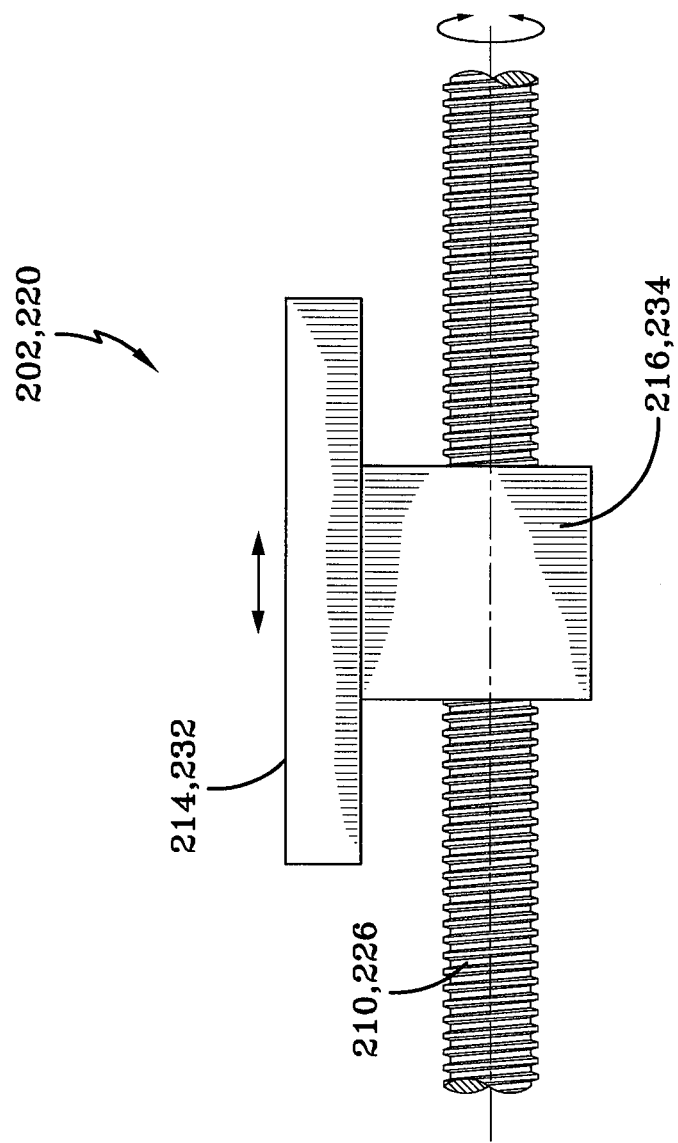
FIG. 10 is a partial schematic view of a rail assembly used in the alternative control mechanism according to the concepts of the present invention.

Referring now to FIGS. 8-10, it can be seen that an alternative, internally maintained control mechanism is designated generally by the numeral 200. In this embodiment, a hull 30' does not require a "rail" bar. Instead, the control mechanism 200 is maintained internally within the hull 30'. As best seen in FIG. 9, the control mechanism 200 provides for a pair of opposed rail assemblies 202 which are mounted to any one of the bars 60 and/or 62 on their internal facing surfaces. As shown in FIG. 9, the opposed rail assemblies 202 are provided with corresponding suffixes A and B to facilitate distinction between the two where that is required. Each of the opposed rail assemblies 202 provide for opposed rails 204A and 204B. At each end of the opposed rails 204 are end caps 206 which maintain the orientation and positioning of the rails with respect to one another. Maintained between the two opposed rails 204 is a lead screw 210 which is mounted between the end caps 206. Each lead screw 210 is journaled at each end with respect to the end cap and, may be provided with a threaded exterior surface. A motor 212 is mounted to one of the end caps 206 for each of the opposed rail assemblies 202. The motor 212 is coupled to the lead screw 210 so as to rotate the lead screw 210 in either a clockwise or counter-clockwise direction. Each motor 212 is connected to the controller 54 and the power compartment 50 to enable operation thereof.

Each opposed rail assembly 202A,B includes a corresponding carriage 214A, B which is slidably mounted upon the opposed rails 204. As best seen in FIG. 10, each carriage 214 provides for a carriage coupling 216, which is received on a corresponding lead screw 210. As such, the motor 212 rotates the corresponding lead screw 210 in either a clockwise or counter-clockwise direction. As a result, the carriage 214 moves along the length of each rail assembly 202. In the embodiment shown, the carriages 214 move in tandem with one another. In other words, the controller 54 sends instructions to the motors 212 so that each lead screw rotates in the same direction at the same time. As a result, both carriages move in the same direction and at the same rate of speed. As will be discussed, this ensures that the weight moves or travels in a desired first direction.

Each carriage 214 supports one end of a cross rail assembly designated generally by the numeral 220. Each cross rail assembly is constructed in a manner similar to the opposed rail assemblies in that the cross rail assembly provides for a pair of opposed cross rails 222. Each end of each cross rail is connected to a cross end cap 224 wherein each end cap 224 is secured to a top side of the corresponding carriage 214. Maintained by the rail assembly 220 is a cross lead screw 226 that is positioned between the opposed cross rails 222. And each end of the cross lead screw 226 is received by a journal in the corresponding end cap 224 to allow rotation of the screw.

A motor 230 is maintained by one of the cross end caps 224 or associated therewith and rotates the cross lead screw 226 in either a clockwise or counter-clockwise direction. A platform 232 is slidably received on the cross rails 222 and a coupling 234 is provided. As with the rail assembly 232, the coupling 234 is associated between the platform 232 and the lead screw 226 such that rotation of the lead screw moves the platform along the length of the cross rail 222. The platform 232 carries a weight 236. And as with the rail assembly 202, the motor 230 is connected to the controller 54 and receives power from the power component 50.

With all of the motors, 230, 212A and 212B connected to the controller, the position of the weight 236 can be adjusted as needed. Accordingly, movement of the weight 236 in the Y direction (a first direction) is obtained by rotating the paired lead screws 210 in tandem and moving the corresponding carriages. When it is desired to move the weight 236 in the X direction (a second direction), the platform 232 is moved as a result of the rotation of the corresponding lead screws 226. As a result, the weight 236 can be moved in two dimensions, which allows for more precise control of the angular orientation of the hull 30'. In other words, instead of adjusting the weight along a single orientation, it will be appreciated that the control mechanism 200 allows for orientation or tilting of the hull 30' in any number of orientations. For example, as shown in FIG. 9, an equilibrium position of the device 30' may be maintained with the weight positioned at about a mid-point of the cross rail assembly 220 and the opposed rail assemblies 202. Moving the weight 236 anywhere along the X-Y grid formed by the rail assemblies 202, 220 imparts a tilt to the device 30'. The amount and direction of tilt can be controlled by positioning the weight predetermined distances away from the equilibrium point.

This embodiment is advantageous in that it is maintained internally within the hull. By moving the weight in two different directions, the ability to tilt the hull in any direction is greatly improved. This embodiment also allows for a way to balance the device if the need arises.

Figure 11:
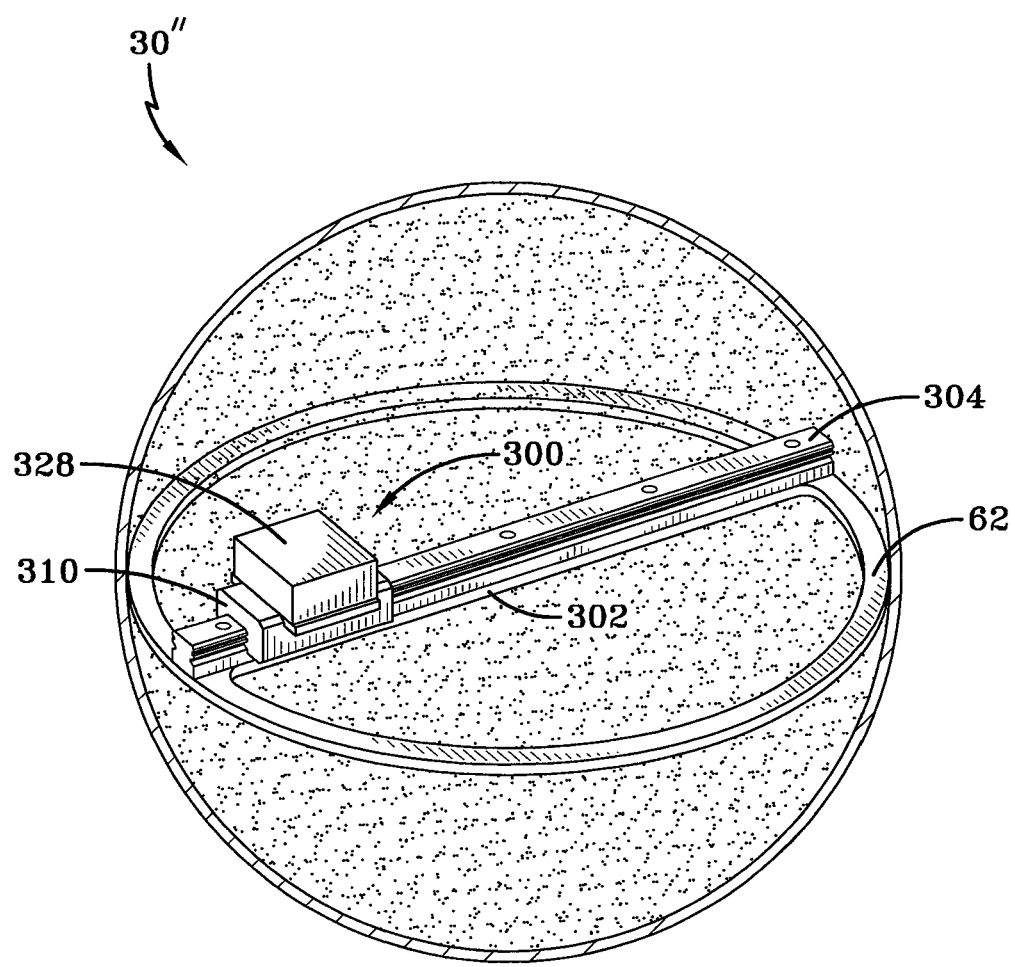
FIG. 11 is a perspective schematic view of an inspection device hull with another alternative control mechanism shown according to the concepts of the present invention.

Referring now to FIGS. 11-15, it can be seen that another alternative, internally maintained, control mechanism is designated generally by the numeral 300. In this embodiment, a hull 30" utilizes a modified bar and maintains the alternative control mechanism 300 internally within the hull 30". As best seen in FIG. 11, the hull 30" is shown in phantom lines to illustrate the positional orientation relationship of the control mechanism with respect to the hull 30". The cage hull 30" provides for a bar 62 with the opening therethrough that is centrally positioned and horizontally oriented. The bar 62 includes a crossbar 302 which bisects the bar's opening. In other words, the crossbar 302 extends across the bar 62 so as to form two symmetrical openings on either side. In some embodiments the bar 62 with the crossbar 302 may have the largest radius of the other horizontally oriented bars, but other bars having a smaller radius may be employed to carry the crossbar 302. In any event, a rail 304 may be secured and/or mounted to the crossbar and, in some embodiments, the rail 304 may be integral with the crossbar.

Figure 12:
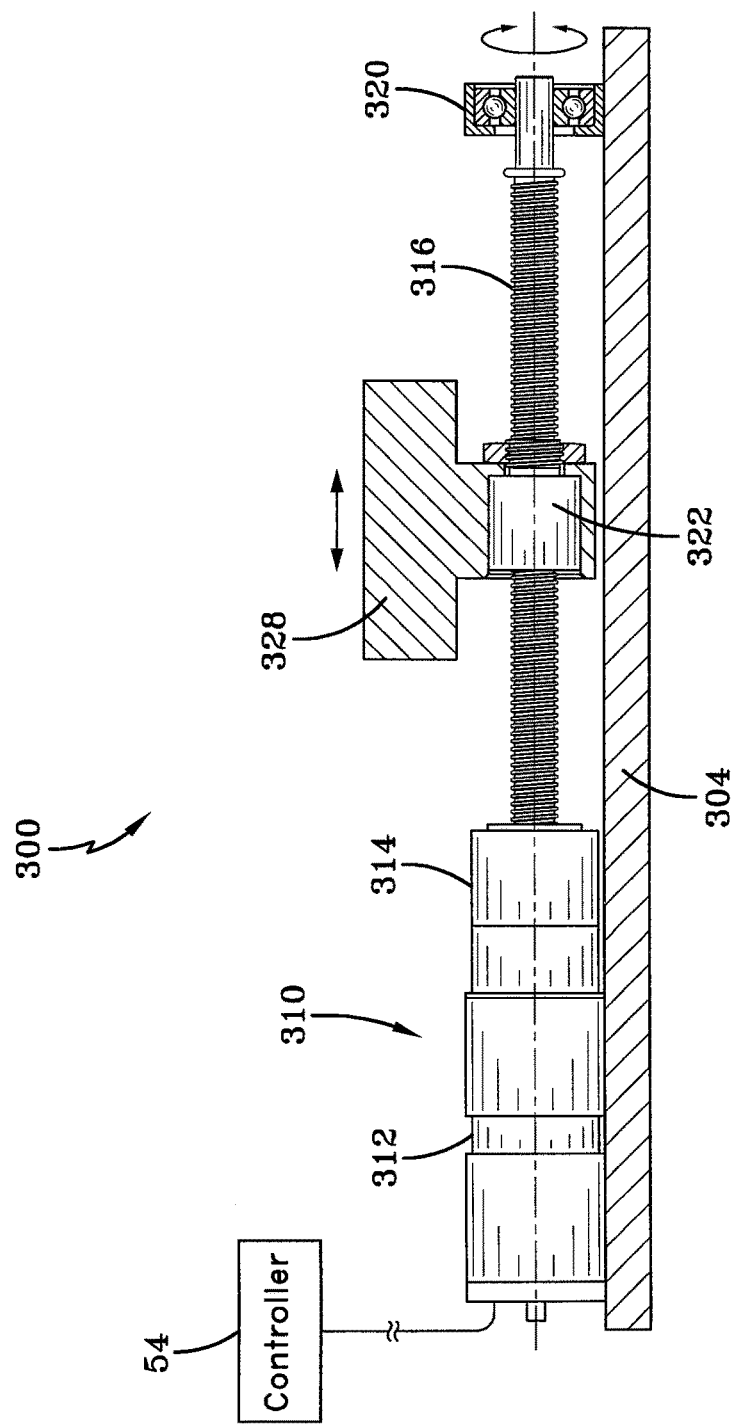
FIG. 12 is an elevational view of the alternative control mechanism according to the concepts of the present invention.

A linear actuator 310, which is schematically represented in FIGS. 11 and 13-15, is mounted to the rail 304 and is utilized for moving a mass from one side of the hull to another. As best seen in FIG. 12, the linear actuator 310, which in some embodiments may be a Faulhaber part # BS22-spindle drive, includes a motor 312 mounted to one end of the rail 304. Coupled to the motor 312 are bearings 314 which rotatably support a lead screw 316 driven by the motor. An opposite end of the lead screw 316 is supported by a bearing 320 which is mounted or supported by the rail 304. Skilled artisans will appreciate that the lead screw 316 is threaded and rotatable in either direction depending upon the rotational direction of a motor shaft rotated by the motor 312. It will further be appreciated that the motor 312 is connected to the controller 54 so as to control operation thereof. Operation of the motor is directed to the direction and speed of rotation of the lead screw which in turn controls the position of the mass.

A carriage coupling 322 is rotatably received on the lead screw 316 and moves laterally as the lead screw is rotated in either direction. A weight 328 is supported and carried by the carriage coupling 322. Accordingly, rotation of the lead screw 316 moves the weight 328 from one end of the lead screw to another. As a result, a mass can be moved internally within the hull 30" so as to adjust the orientation of the hull 30" within a fluid.

Figure 13:
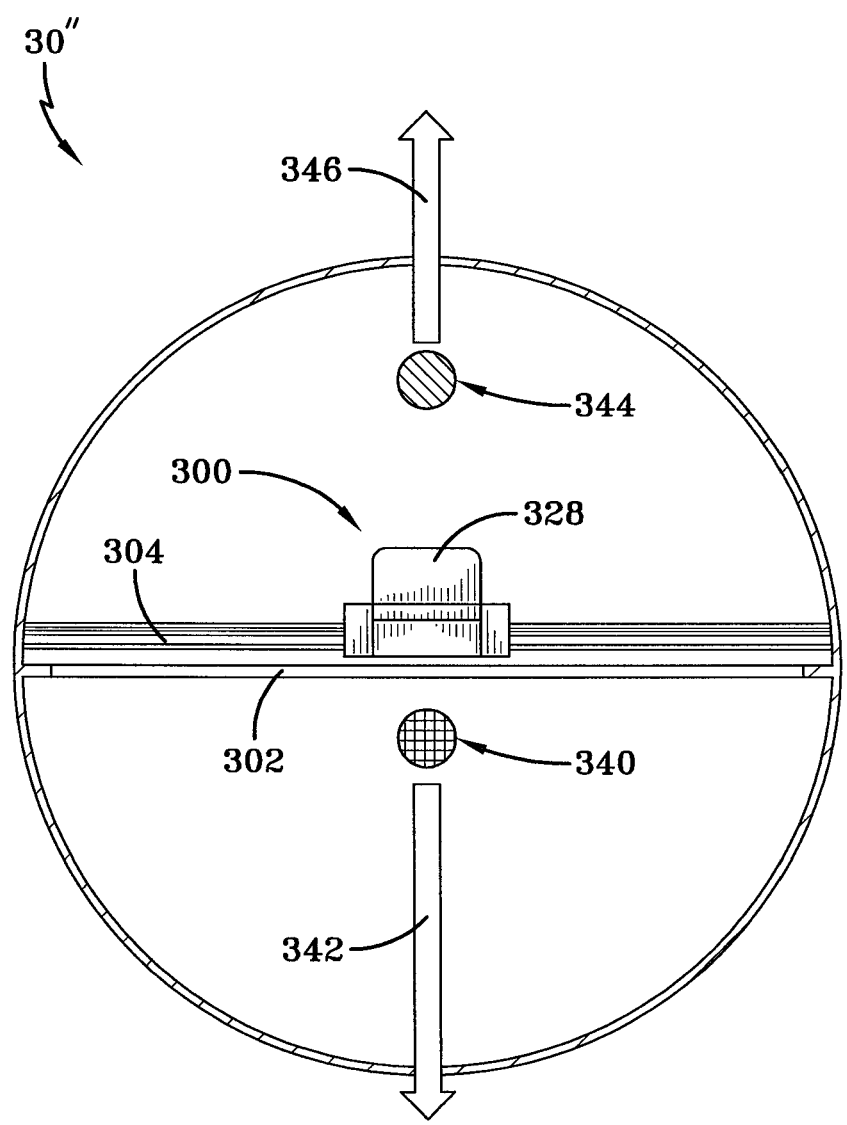
FIG. 13 is a schematic representation of the hull shown in a substantially horizontal orientation with the alternative control mechanism according to the concepts of the present invention.
Figure 14:
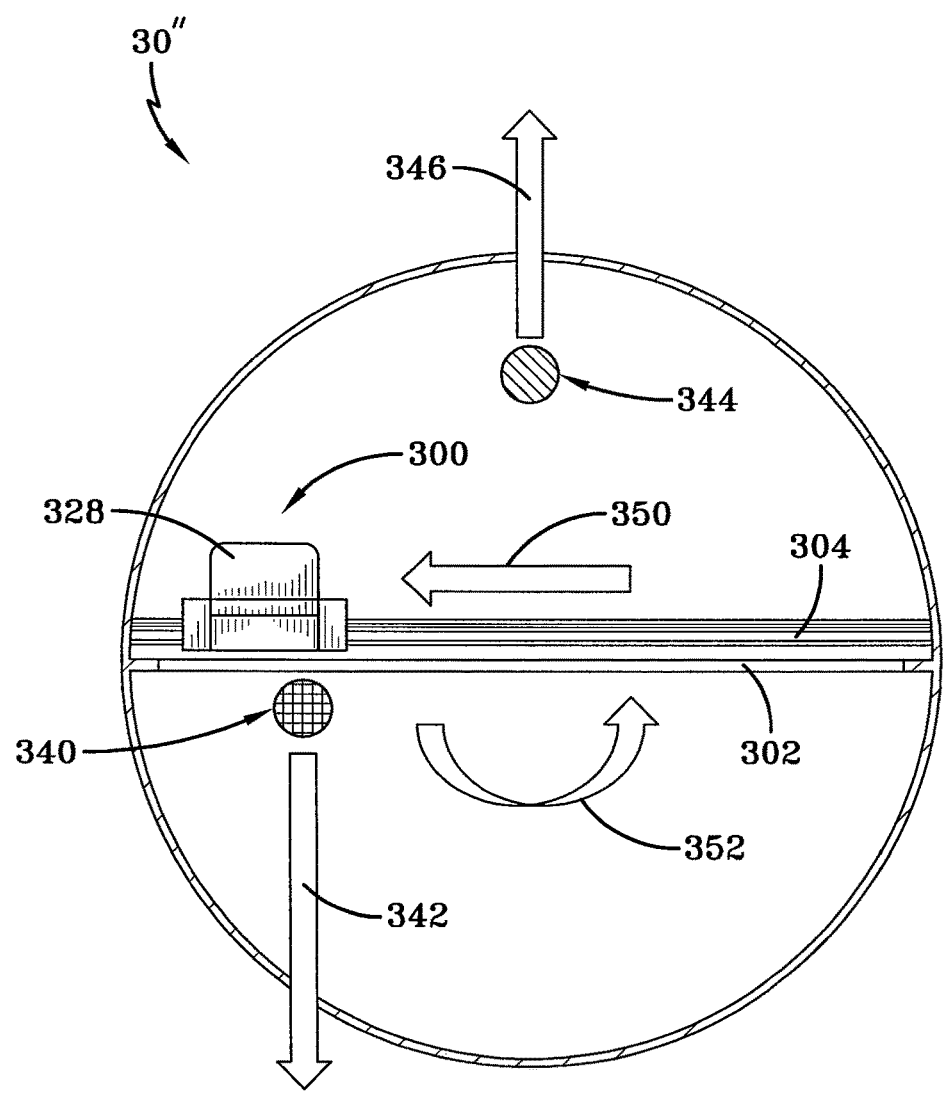
FIG. 14 is a schematic representation of the hull with the alternative control mechanism showing the shifting of a weight to a tilting position according to the concepts of the present invention.
Figure 15:
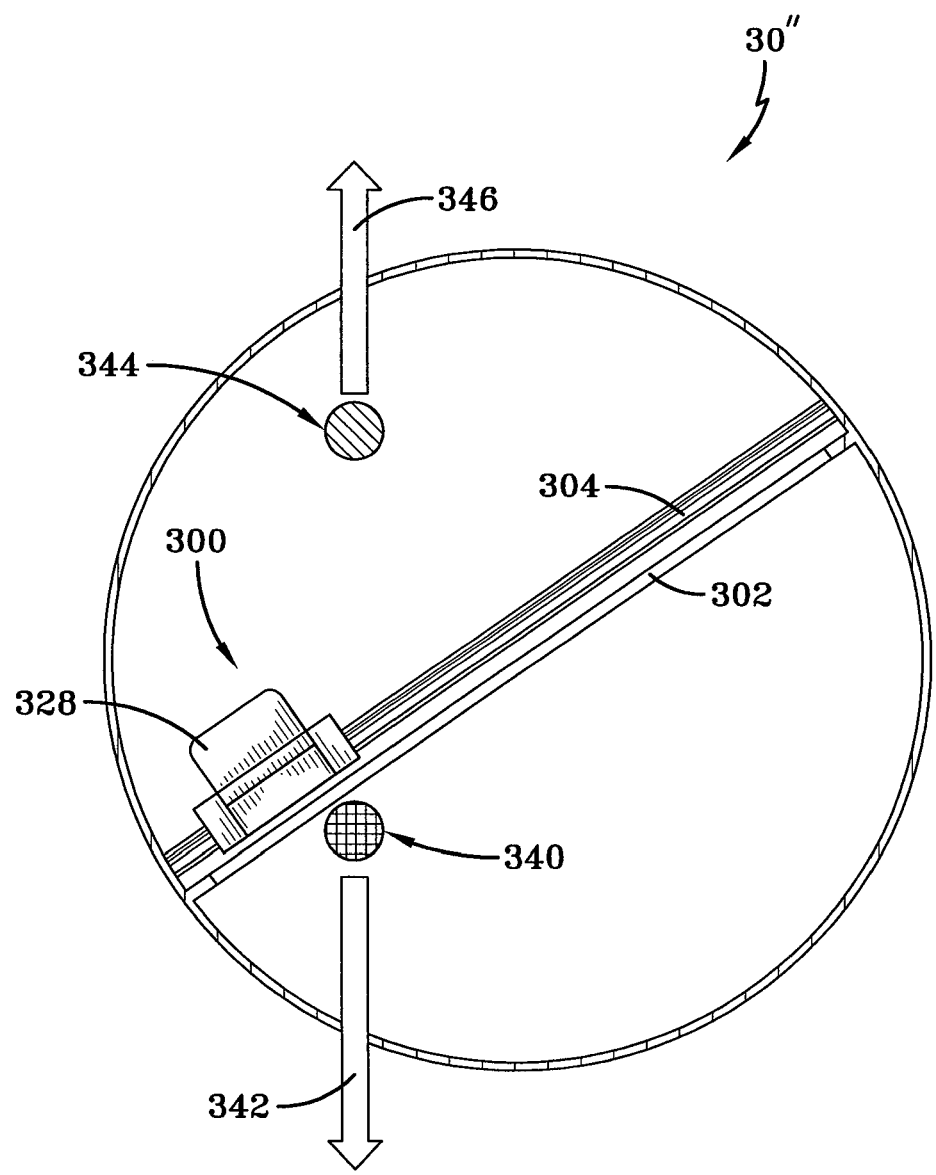
FIG. 15 is a schematic representation of the hull with the alternative control mechanism shown in a tilted equilibrium position according to the concepts of the present invention.

Referring now to FIGS. 13-15, the movement of the weight 328 and its effects will be described. FIG. 13 shows the weight 328 maintained in a relatively central position with respect to the cage hull 30". Also shown in FIG. 13 is a representation of the center of gravity 340 and an associated gravitational force 342 which is directed downwardly. Also shown is a center of buoyancy 344 and its associated buoyancy force 346. As previously described, the linear actuator 310 can be used to shift the weight 328, which in turn shifts a portion of the mass of the hull, thus changing the position of the center of gravity. Whenever the center of gravity of a submersible object, such as the hull 30", is not directly below the center of buoyancy (which remains stable in the present embodiment) there is a righting moment driving the craft to rotate to align the center of gravity directly below the center of buoyancy.

As seen in FIG. 14, movement of a weight shifting force 350—when the weight 325 is moved from a central position to an outer position—results in the aforementioned generation of a moment force 352. As a result, the center of gravity 340 shifts to a position somewhat aligned with the weight 328 and, as a result, the gravitational force 342 is likewise shifted. During this weight shifting process, the hull 30″ will begin to reorient itself until the center of buoyancy 244 aligns with the center of gravity affecting the rotation of the craft. As a result, placement of the movable mass along the rail 302 anywhere within the hull 30″ results in the creation of a righting moment, thus driving the hull to reorient itself until the center of gravity is directly below the center of buoyancy. Accordingly, the linear motion of the weight adjusts the center of gravity so that a desired tilt of the hull may be obtained. Accordingly, the tilt orientation of the hull 30″ can be adjusted as needed in order to orient the sensor, such as the camera, to a desired line of sight.

This embodiment is advantageous in that the control mechanism is of a minimal size and can be maintained within the hull 30″ with minimal use of critical internal space that can be used for other components. Such a device allows for tilting in a particular direction; however, rotational orientation of the hull 30″ must be accomplished utilizing the appropriate thruster mechanism maintained by the hull 30″.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. An inspection device for use in a fluid container, comprising:
   a hull adapted to be received in the fluid container;
   a control mechanism carried by said hull, said control mechanism movably positioning a weight about said hull so as to adjust an angular orientation of said hull within the fluid container; and
   a propulsion mechanism to move said hull, wherein said propulsion mechanism is disposed entirely inside said hull and operative to propel said hull.

2. The device according to claim 1, wherein said control mechanism adjusts said hull's orientation without activation of said propulsion mechanism.

3. The device according to claim 1, wherein said control mechanism is carried in a predetermined orientation by said hull and wherein said weight is movable about said predetermined orientation.

4. The device according to claim 3, wherein said weight is moved about in a single plane maintained by said hull.

5. The device according to claim 3, wherein said hull comprises:
   at least two bars, each said bar providing an opening wherein said opening forms a cage cavity and wherein said control mechanism comprises a rail carried by one of said bars.

6. The device according to claim 5, wherein said rail is hemispherically disposed about said hull.

7. The device according to claim 3, wherein said control mechanism comprises:
   a controller;
   a motor connected to said controller; and
   said motor coupled to said weight, wherein said controller operates said motor to move said at least one weight about said hull so as to move said hull's orientation.

8. The device according to claim 7, wherein said control mechanism further comprises:
   a loop coupled to said weight; and
   at least one motor wheel rotated by said motor, said at least one motor wheel coupled to said loop, wherein rotation of said at least one motor wheel moves said loop which in turn moves said weight.

9. An inspection device for use in a fluid container, comprising:
   a hull adapted to be received in the fluid container; and
   a control mechanism carried by said hull, said control mechanism movably positioning a weight about said hull so as to adjust an angular orientation of said hull within the fluid container,
   wherein said hull comprises a plurality of bars and wherein one of said plurality of bars is a rail that slidably receives said at least one weight.

10. The device according to claim 9, wherein said rail has opposed bar grooves which receive a loop that has each end connected to corresponding ends of said at least one weight.

11. The device according to claim 1, wherein said control mechanism is maintained internally within said hull.

12. An inspection device for use in a fluid container, comprising:
   a hull adapted to be received in the fluid container; and
   a control mechanism carried by said hull, said control mechanism movably positioning a weight about said hull so as to adjust an angular orientation of said hull within the fluid container,
   wherein said control mechanism is maintained internally within said hull, and
   wherein said control mechanism further comprises:
   a pair of opposed rail assemblies;
   a cross rail assembly slidably mounted on said pair of opposed rail assemblies;
   wherein said at least one weight is carried by said cross rail assembly.

13. The device according to claim 12, wherein each said pair of rail assemblies comprises:
   a pair of opposed rails having an end cap at each end;
   a lead screw rotatably mounted between each said end cap; and
   a carriage slidably coupled to said pair of opposed rails and coupled to said lead screw.

14. The device according to claim 13, wherein said cross rail assembly is mounted on said carriages.

15. The device according to claim 14, wherein said cross rail assembly comprises:
   a pair of opposed cross rails having a cross end cap at each end;
   a cross lead screw rotatably mounted between each said end cap;
   a platform slidably coupled to said pair of opposed cross rails and coupled to said cross lead screw, and wherein said at least one weight is mounted on said platform.

16. The device according to claim 15, further comprising:
   a motor connected to each said lead screw to move said carriage along said pair of opposed rails; and
   a cross motor connected to said cross lead screw to move said platform along said pair of opposed cross rails.

17. The device according to claim 11, wherein said hull comprises:

a plurality of bars, wherein each said bar has an opening therethrough and at least one of said plurality of bars is oriented substantially horizontally; and a crossbar spanning said opening and connected at each end to said horizontally oriented bar, wherein said control mechanism is carried by said crossbar.

18. The device according to claim 17, wherein said control mechanism further comprises:

a linear actuator carried by said rail, said linear actuator having a motor that rotates a lead screw, said lead screw moving said weight.

19. The device according to claim 18, wherein said control mechanism further comprises a carriage coupling which moves linearly as said lead screw is rotated, and wherein said weight is mounted on said carriage coupling.

20. The device according to claim 1, wherein the fluid container is a transformer tank containing a transformer and a dielectric transformer cooling fluid; wherein the hull is adapted for operation in the dielectric transformer cooling fluid and for operation adjacent to the transformer in the transformer tank; and wherein the inspection device is constructed for inspection of the transformer.

* * * * *